US012760269B2

(12) United States Patent
Liu et al.

(10) Patent No.: US 12,760,269 B2
(45) Date of Patent: Oct. 13, 2026

(54) BIOLOGICAL REACTION DEVICE AND CULTURE METHOD FOR ADVENTITIOUS ROOTS OF *PANAX GINSENG* C. A. MEY

(71) Applicant: SHANGHAI KODILIN TECHNOLOGY CO., LTD, Shanghai (CN)

(72) Inventors: Bing Liu, Weihai (CN); Mingchen Zhang, Weihai (CN); Xiujun Gao, Weihai (CN); Peisheng Yan, Weihai (CN)

(73) Assignee: Shanghai Kodilin Technology Co., Ltd, Shanghai (CN)

( * ) Notice: Subject to any disclaimer, the term of this patent is extended or adjusted under 35 U.S.C. 154(b) by 708 days.

(21) Appl. No.: 18/262,780

(22) PCT Filed: Mar. 18, 2022

(86) PCT No.: PCT/CN2022/081650
§ 371 (c)(1),
(2) Date: Jul. 25, 2023

(87) PCT Pub. No.: WO2022/206423
PCT Pub. Date: Oct. 6, 2022

(65) Prior Publication Data

US 2024/0409887 A1 Dec. 12, 2024

(30) Foreign Application Priority Data

Apr. 2, 2021 (CN) ......................... 202110361956.4

(51) Int. Cl.
*C12N 5/04* (2006.01)
*C12M 1/00* (2006.01)
(Continued)

(52) U.S. Cl.
CPC ............... *C12N 5/04* (2013.01); *C12M 23/02* (2013.01); *C12M 23/22* (2013.01); *C12M 23/38* (2013.01);
(Continued)

(58) Field of Classification Search
CPC .......... A01H 4/00; A01H 4/001; A01H 4/008; A01H 6/00; C12M 23/02; C12M 23/22;
(Continued)

(56) References Cited

FOREIGN PATENT DOCUMENTS

CA 2276003 A1 * 12/1999 ............... A01H 4/00
CN 104509441 A 4/2015
(Continued)

OTHER PUBLICATIONS

Yu, Dan et al. "Mass Production of Adventitious Roots of Oplopanax elatus in Bioreactor" (Chinese Agricultural Science Bulletin), vol. 30, No. 16, Jun. 5, 2014 (Jun. 5, 2014).
(Continued)

*Primary Examiner* — Michael L Hobbs
(74) *Attorney, Agent, or Firm* — Sand, Sebolt & Wernow Co., LPA

(57) ABSTRACT

The present disclosure discloses a biological reaction device and a culture method for adventitious roots of *Panax ginseng* C. A. MEY. The biological reaction device includes a tank body, wherein the top of the tank body is provided with a cover body which can be opened and closed, and a bottom of the tank body is provided with at least two air inlet devices. The method includes washing and disinfecting mature ginseng, cutting the disinfected ginseng into slices, inoculating the ginseng slices into an induction medium to induce ginseng adventitious roots, re-inoculating the ginseng adventitious roots into an induction medium for subculture and propagation, then inoculating the obtained ginseng adventitious roots into a shake flask containing a liquid
(Continued)

medium for dark culture, and then inoculating the obtained ginseng adventitious roots into a biological reaction device containing a liquid medium for culture to obtain ginseng adventitious roots.

19 Claims, 2 Drawing Sheets

(51) Int. Cl.
*C12M 1/12* (2006.01)
*C12M 3/00* (2006.01)

(52) U.S. Cl.
CPC ............ *C12M 23/48* (2013.01); *C12M 29/22* (2013.01); *C12M 37/02* (2013.01)

(58) Field of Classification Search
CPC ...... C12M 23/38; C12M 23/48; C12M 29/02; C12M 37/02; C12N 5/04
See application file for complete search history.

(56) References Cited

FOREIGN PATENT DOCUMENTS

| | | | | | |
|---|---|---|---|---|---|
| CN | 201410698528 | A | | 4/2015 | |
| CN | 104509441 | | * | 1/2017 | .............. C12M 3/02 |
| CN | 201711459037.0 | A | | 7/2018 | |
| CN | 108522247 | A | | 9/2018 | |
| CN | 110476804 | A | | 11/2019 | |
| CN | 112931216 | A | | 6/2021 | |
| JP | H0220281 | A | | 1/1990 | |
| KR | 100666879 | B1 | | 1/2007 | |

OTHER PUBLICATIONS

Hao, Yuejun et al. "Study on Growth Dynamic of Panax Ginseng Adventitious Roots and the Determination of Active Substance Contents Under Two Culture Conditions" (Agricultural Science Journal of Yanbian University), vol. 42, No. 2, Jun. 30, 2020 (Jun. 30, 2020).

Jung-Yeon Han et al. Induction of Adventitious Roots and Analysis of Ginsenoside Content and the Genes Involved in Triterpene Biosynthesis in Panax ginseng Journal of Plant Biology, vol. 49, No. 1, Feb. 28, 2006 (Feb. 28, 2006).

Sung Mee Choi, et al: "Pilot-scale culture of adventitious roots of ginseng in a bioreactor system", Apr. 18, 2000 (Apr. 18, 2000), Plant Cell, Tissue, and Organ Culture, v.62, p. 187-193, KluwerAcademic Publishers, Printed in the Netherlands, XP093171076.

Hosakatte Niranjana Murthy, et al: Tools for biotechnological production of useful phytochemicals from adventitious root cultures' Phytochemistry Reviews,Kluwer, NL, vol. 15,No. 1, Dec. 11, 2014 (Dec. 11, 2014),pp. 129-145, XP035706774. ISSN:1568-7767,DO1:10.1007/S11101-014-9391-Z [retrieved on Dec. 11, 2014].

Hosakatte Niranjana Murthy, et al: "Panax ginseng Adventitious Root Suspension Culture: Protocol for Biomass Production and Analysis of Ginsenosides by High Pressure Liquid Chromatography" ln:"Protocols for In Vitro Cultures and Secondary Metabolite Analysis of Aromatic and Medicinal Plants, Second Edition", Jan. 1, 2016 (Jan. 1, 2016),Springer New York, XP093171080ISSN:1064-3745 vol. 1391,pp. 125-139, DOI:10.1007/978-1-4939-3332-7 9. Retrieved from the internet:URL:http://linkspringer.com/content/.

Xianfu Gao et al: "Induction and Characterization of Adventitious Roots Directly from the Explants of Panax notoginseng" Biotechnology Letters, Springer Netherlands, Dordrecht. vol. 27,No. 22, Sep. 1, 2005(Sep. 1, 2005), pp. 1771-1775, XP019231041,ISSN:1573-6776,DO1:10.1007/S10529-005-3553-4.

Yue Zhao et al: "A culture system for the stable and high-efficiency proliferation of adventitious roots of Panax notoginseng and ginsenoside accumulation" Industrial Crops and Products, Elsevier, NLvol. 157, Sep. 21, 2020(Sep. 21, 2020), XP086319208ISSN:0926-6690,DO1:10.1016/J.INDCROP.2020.112882[retrieved on Sep. 11, 2020.

* cited by examiner

BIOLOGICAL REACTION DEVICE AND CULTURE METHOD FOR ADVENTITIOUS ROOTS OF *PANAX GINSENG* C. A. MEY

FIELD

The present disclosure belongs to the technical field of plant tissue culture, and in particular relates to a biological reaction device and a culture method for adventitious roots of *Panax ginseng* C. A. Mey.

BACKGROUND

Ginseng (*Panax ginseng* C. A. Mey) is a plant of the genus *Panax* of Araliaceae, distributed in China, Japan, and Korea, and its rhizome is a precious Chinese medicinal material, known as the "king of herbs". Ginseng tastes sweet and slightly bitter, and is slightly warm. It has the effects of reinforcing vital energy, restoring the pulse for relieving desertion, tonifying the spleen and benefiting the lung, promoting fluid production and nourishing blood, calming the nerves and improving the intelligence. It is mainly used for verging on desertion due to weak health, reducing appetite due to spleen deficiency, asthma and cough due to lung deficiency, thirst due to body fluid deficiency, insomnia due to palpitation, etc. Ginsenoside is the main active ingredient of ginseng, which has the effects of antifatigue, delaying aging, regulating the central nervous system, improving the immunity of the body, improving the blood supply insufficiency of heart and cerebral vessels, and inhibiting the production of tumor cells. In recent years, ginseng has been widely used in various cosmetics, health care products and drinks, and the market prospect of ginseng is very broad.

At present, wild ginseng resources are almost extinct due to excessive digging, environmental destruction, etc., and field cultivation is the main source of ginseng. However, ginseng grows slowly, has a long planting period, and requires strict environmental conditions. Its quality is easily affected by climate, cultivation conditions, diseases and insect pests. Its cultivation techniques are complex, and there are also problems such as excessive pesticide residues and old ginseng soil. These problems greatly limit the development prospects of artificial cultivation of ginseng. The supply of ginseng cultivated in the field is difficult to meet the market demand. Ginseng tissue culture technology has a short cycle, is not limited by seasons, and is prone to large-scale industrial production, which has a great development prospect.

However, on one hand, at present, adventitious roots are generally induced by ginseng callus, which needs to induce callus first and then induce adventitious roots, which requires a long experimental cycle, and has complex operation steps and high pollution risk. On the other hand, there is also a problem that the content of ginsenoside in cultivated ginseng is low and unstable, which is difficult to meet the application requirements.

Chinese patent application No. CN201711459037.0 discloses a method for tissue culture of wild ginseng adventitious roots, which comprises the steps: (1) induction of wild ginseng callus; (2) proliferation of the wild ginseng callus; (3) induction of wild ginseng adventitious roots; (4) proliferation of the wild ginseng adventitious roots in a liquid medium. In the above technical solution, the callus need to be induced first, and then the adventitious roots are induced, which requires a long cycle and a complex process and has a low content of ginsenoside.

Chinese patent application No. 201410698528.0 discloses a method for inducing the proliferation of ginseng adventitious roots, which comprises the following steps: cutting ginseng tissue culture seedlings into small tissue pieces, inoculating the small tissue pieces into a solid induction medium to induce formation of adventitious roots; cutting the adventitious roots into small adventitious root pieces, and inoculating the small adventitious root pieces into a liquid proliferation medium for proliferation culture of adventitious roots; wherein the solid induction medium and the liquid proliferation medium use a ½ MS (–N) medium as a minimal medium, and contains 1-10 mg/L of indole-butyric acid. In the above solution, the tissue culture seedlings of 28-32 days old are cut into small pieces to directly induce adventitious roots, the tissue culture seedlings are young and tender, and have strong differentiation ability. In fact, it takes at least 28-32 days to obtain tissue culture seedlings through seed germination or explant culture, and explant culture still needs callus induction. Thus, the cycle is not actually shortened.

In order to obtain a large number of ginseng adventitious roots, in the prior art, a biological reaction device can be used for expanded culture. However, the existing biological reaction device has a complex structure, uneven ventilation and inconvenient operation.

In view of this, the present disclosure is specifically proposed.

SUMMARY

The technical problem to be solved by the present disclosure is to overcome the deficiencies in the prior art and provide a biological reaction device and a culture method for adventitious roots of ginseng. An improved biological reaction device of the present disclosure is a small simple bioreactor with a simple structure, uniform ventilation, and easy operation, and is suitable for producing ginseng adventitious roots anytime and anywhere by manual operation, and the adventitious roots grow quickly.

In order to solve the above technical problem, a basic idea of the technical solution adopted by the present disclosure is as follows:

a first object of the present disclosure is to provide a biological reaction device for cultivation of ginseng adventitious roots, including a tank body, wherein a top of the tank body is provided with a cover body which can be opened and closed, and an air discharge device is arranged on the cover body or at the top of the tank body; and a bottom of the tank body is provided with at least two air inlet devices, and allowing air to enter the tank through the at least two air inlet devices.

The biological reaction device of the present disclosure is a small bioreactor with a simple structure and easy operation. The biological reaction device can be used to produce adventitious roots of ginseng conveniently, and the adventitious roots grow quickly and the growth multiple is high.

In the present disclosure, the tank body is hollow inside for holding a liquid medium. The biological reaction device can be made of any material suitable for manufacturing a fermenter that can be used for high-temperature sterilization, e.g., glass, stainless steel, high temperature resistant plastic, etc.; preferably, stainless steel, which is durable and has a long service life. The cover body at the top of the tank body can be opened or closed for adding a liquid medium into the tank body, and the cover body is in sealed connection with the tank body after the liquid medium is added. The bottom of the tank body is provided with at least two air inlet devices, and sterile air is introduced into the tank body from different positions, so as to ensure that a culture in the tank body can be in full contact with the air and grows evenly, which is conducive to promoting the rapid growth of adventitious roots.

In a further solution, the biological reaction device according to the present disclosure has a volume of 1-500 L, preferably 1-50 L, preferably 2-20 L, preferably 3-10 L, preferably 5 L.

In a further solution, a center of the bottom of the tank body is provided with a discharge opening, and the air inlet devices are evenly distributed around the discharge opening at intervals; and preferably, a height of a bottom wall of the tank body is gradually decreased from the periphery to the center to form an inverted cone with a large upper part and a small lower part; and the discharge opening is formed at the lowest position of the center of the bottom of the tank body, and the air inlet devices are evenly distributed around the discharge opening at intervals on the bottom wall of the tank body gradually decreasing from the periphery to the center.

In the present disclosure, the air inlet devices are arranged on inclined planes of the bottom wall of the tank body, the bottom wall of the tank body being of the inverted cone with the large upper part and the small lower part, so that inlet air will not rise vertically. Further, two or more air inlet devices are evenly distributed around the center at intervals, which is conducive to uniform distribution of air in the tank body and uniform growth of adventitious roots in the tank body.

Further, the biological reaction device of the present disclosure further includes a support structure for supporting the tank body to be placed vertically on a plane. In particular, the support structure includes support feet which are connected to or disposed integrally with a lower part of the tank body, and the tank body is placed on a plane or platform by means of the support feet. Preferably, the conical bottom of the tank body is located within a space enclosed by the support feet.

In a further solution, each of the air inlet devices includes an air inlet, an air inlet pipe and an air filter, the air inlet is located on the bottom wall of the tank body, the air inlet pipe is connected to the air inlet in sealing manner, and the air filter is disposed in the air inlet pipe to filter air passing through the air inlet pipe.

In a further solution, the air discharge device includes an exhaust port, an exhaust pipe and a filter device, the exhaust port is arranged on the cover body or on the top of the tank body, the exhaust pipe is connected with the exhaust port in sealing manner, and the filter device is disposed in the exhaust pipe; and preferably, the filter device is an air filter or a liquid filter.

As one preferred embodiment, the exhaust port is formed in the center of the cover body.

In the above solution, when the filter device disposed on the exhaust pipe is an air filter, external air can be prevented from entering the tank body from the top, ensuring a sterile culture environment inside the tank body. In addition, liquid can be added from the top when the filter device on the exhaust pipe is replaced with a liquid filter.

Further, an inoculation port is arranged on the cover body or on the top of the tank body for inoculation.

In a further solution, the tank body is provided with a plurality of viewing windows of transparent; and preferably, the viewing windows are arranged on a side wall of a middle part and/or a lower part of the tank body.

When the tank body is made of opaque stainless steel, the interior of the tank body can be viewed from different angles through the plurality of the viewing windows of transparent arranged at different positions to timely grasp the growth of ginseng adventitious roots inside the tank body.

In a further solution, the tank body is also provided with a handle; and preferably, at least two handles are provided.

The handles arranged on the tank body may be symmetrically arranged, which is convenient for users to conveniently take and move the biological reaction device.

A second object of the present disclosure is to provide a method for culturing adventitious roots of ginseng by using a biological reaction device, including:

(1) washing and disinfecting mature ginseng, cutting the mature ginseng disinfected into ginseng slices, and inoculating the ginseng slices into an induction medium to induce adventitious roots of ginseng;

(2) re-inoculating the adventitious roots of ginseng obtained in step (1) into an induction medium for subculture and propagation;

(3) inoculating the adventitious roots of ginseng obtained in step (2) into a shake flask containing a liquid medium for dark culture; and step (4) then inoculating the adventitious roots of ginseng obtained in step (3) into the biological reaction device described in any one or a combination of the above solutions containing a liquid medium for culture to obtain adventitious roots of ginseng.

At present, adventitious roots are generally induced by ginseng callus, which needs to induce callus first and then induce adventitious roots, which requires a long experimental cycle, and has complex operation steps and high pollution risk. In addition, there is also a problem that the content of ginsenoside in cultivated ginseng is low, which is difficult to meet the needs of clinical applications.

In view of the long age, high maturity and difficulty in differentiation of mature ginseng, there is no report that adventitious roots can be directly induced from mature ginseng. After a large number of experiments, the present disclosure unexpectedly found that adventitious roots can be directly induced from mature ginseng slices in a specific induction medium, so that the adventitious roots can be directly induced from the mature ginseng in one step without an intermediate step of callus induction, thereby simplifying the induction steps and shortening the induction time.

In a further solution, in the steps (1) and (2), the induction medium includes 1-6 mg/L of naphthylacetic acid, 0.1-0.6 mg/L of kinetin, 0.2-1 mg/L of gibberellin, 0.075-1.5 g/L of citric acid, 0.03-1 g/L of ascorbic acid, 20-60 g/L of sucrose, 1-6 g/L of Phytagel, 1-4 g/L of a B5 medium and 1-2.4 g/L of a WPM medium.

The induction medium in the above solution enables direct induction of adventitious roots from the parts of the mature ginseng without the intermediate step of callus induction, thereby simplifying the induction steps and shortening the induction time.

In this solution, naphthylacetic acid is a plant growth regulator and gibberellin is a plant hormone, which can both promote adventitious root formation. Kinetin is a cytokinin that can promote division of cells. Citric acid and ascorbic acid can produce synergistic antioxidant effects, prevent browning of mature ginseng tissue in vitro, and facilitate direct induction of adventitious roots from the mature ginseng tissue in vitro. The ingredients in the induction medium act synergistically, eventually achieving direct induction of adventitious roots from the parts of the mature ginseng without the intermediate step of callus induction.

In a further solution, the induction medium includes 4 mg/L of naphthylacetic acid, 0.6 mg/L of gibberellin, 0.4 mg/L of kinetin, 0.1 g/L of citric acid, 0.05 g/L of ascorbic acid, 30 g/L of sucrose, 3 g/L of Phytagel, 1.55 g/L of a B5 medium and 1.21 g/L of a WPM medium.

The induction medium in the above ratio of ingredients has the best effect on the induction of adventitious roots from mature ginseng. The number of the produced adventitious roots is large and the quality is good, which is conducive to next propagation, and increases the content of active ingredients in adventitious roots.

In a further solution, in the step (3), the liquid medium includes a basic medium selected one or more one medium from a group containing a B5 medium, a WPM medium and a ½ MS medium, and 4 mg/L of indolebutyric acid, and 30 g/L of sucrose; and preferably, the liquid medium further includes 0.1 g/L of citric acid, and 0.05 g/L of ascorbic acid.

In the present disclosure, when further liquid culture is carried out on the induced adventitious roots, a conventional medium, such as a ½ MS medium, can be adopted, which is consistent with the commonly used adventitious root medium. The adventitious roots induced by the one-step method of the present disclosure can be cultured in the conventional liquid medium, and meanwhile, the induction time is shortened and the pollution risk is reduced.

In a further solution, the slices are thin slices having a width of 0.5-0.7 cm, a length of 0.5-0.7 cm, and a thickness of 0.2-0.5 mm.

In a further solution, in the step (3), a volume of a sterilized liquid medium is 20%-80% of a volume of the biological reaction device, preferably 30%-70%;

in a further solution, the adventitious roots are inoculated into the liquid medium at an inoculation amount of 0.2-3%, preferably 0.7-1%;

in a further solution, the biological reaction device is fed with filtered air by air inlet devices at an air feeding amount of 0.02-0.5 vvm, preferably 0.02-0.3 vvm; and in a further solution, the dark culture is conducted at 22±1° C. for 4-5 weeks in the biological reaction device.

In a further solution, a method for culturing ginseng adventitious roots includes the steps of:

(1) washing and disinfecting mature ginseng, cutting the disinfected ginseng into slices, and inoculating the ginseng slices into an induction medium for dark culture at 22±1° C. for 4-5 weeks to induce adventitious roots of ginseng;
(2) inoculating the adventitious roots of ginseng obtained in the step (1) into the same induction medium as that in the step (1) for dark culture under the same conditions for 4-5 weeks;
(3) inoculating the adventitious roots of ginseng obtained in the step (2) into a liquid medium for dark culture at 100-140 rpm at 22±1° C. for 3-4 weeks; and
(4) cutting the adventitious roots of ginseng obtained in the step (3) into small segments, and inoculating the small adventitious root of ginseng segments into a liquid medium of the biological reaction device at an inoculation amount of 0.2-3% for culture at 22±1° C. for 3-4 weeks to obtain adventitious roots.

In a further solution, the mature ginseng has an age of 3 years or more; preferably, the mature ginseng has an age of 6 years or more; and as one preferred embodiment, the mature ginseng is centennial ginseng. The centennial ginseng is very rare in nature, and has a high edible and medicinal value, and can nourish the five internal organs, soothe the nerves, calm the soul, stop palpitation, eliminate evil spirits, improve eyesight, and make happy and improve intelligence. And its value is much greater than that of planted ginseng with a short age. The present disclosure does not require the intermediate step of callus induction, adventitious roots can be directly induced from centennial ginseng slices in one step, which can not only simplify the induction steps, and shorten the induction time, but also obtain unique functional components in the female parent centennial ginseng, thereby obtaining adventitious roots with better nutritional values.

In a further solution, taproots, or rhizomes, or adventitious roots on rhizomes, or lateral roots, or fibrous roots of the mature ginseng are washed and disinfected, sliced and inoculated into an induction medium to induce adventitious roots of ginseng.

In a further solution, the ginseng is selected from wild ginseng, transplant wild ginseng, ginseng under forest, and garden ginseng; and preferably, the ginseng is wild ginseng.

As one specific preferred embodiment, culturing adventitious roots according to the present disclosure specifically includes the following steps:

(1) induction of adventitious roots taproots of mature ginseng are washed and sterilized, cut into slices having a width of 0.5-0.7 cm, a length of 0.5-0.7 cm, and a thickness of 0.2-0.5 mm, and inoculated into an induction medium containing 4 mg/L of naphthylacetic acid, 0.6 mg/L of gibberellin, 0.4 mg/L of kinetin, 0.1 g/L of citric acid, 0.05 g/L of ascorbic acid, 30 g/L of sucrose, 3 g/L of Phytagel, 1.55 g/L of a B5 medium and 1.21 g/L of a WPM medium for dark culture at 22±1° C. for 4-5 weeks to induce ginseng adventitious roots;

(2) subculture of adventitious roots the ginseng adventitious roots obtained in the step (1) are inoculated into the same induction medium as that in the step (1) for dark culture under the same conditions for 4-5 weeks;

20) (3) culture of adventitious roots in a shake flask the ginseng adventitious roots obtained in the step (2) are inoculated into a shake flask filled with a liquid medium for dark culture at 22±1° C. for 3-4 weeks; wherein the liquid medium contains 4 mg/L of indolebutyric acid, 0.1 g/L of citric acid, 0.05 g/L of ascorbic acid, a ½ MS medium, and 30 g/L of sucrose; and (4) culture of adventitious roots in a biological reaction device the ginseng adventitious roots obtained in the step (3) are cut into tissue of about 1-2 cm in length, and inoculated into a liquid medium in a biological reaction device at an inoculation amount of 0.2-3%, wherein a volume of the liquid medium is 30-70% of a volume of the biological reaction device; and the liquid medium contains 4 mg/L of indolebutyric acid, 0.1 g/L of citric acid, 0.05 g/L of ascorbic acid, a ½ MS medium and 30 g/L of sucrose, dark culture is conducted at 22±1° C. for 3-4 weeks to obtain adventitious roots, and the biological reaction device is fed with filtered air by the air inlet devices at an air feeding amount of 0.02-0.5 vvm.

In a further solution, the pH of the induction medium or the liquid medium of the present disclosure is 5.6-6.0. In addition, in order to increase the content of ginsenoside in the adventitious roots of ginseng, the inventors further perform screening optimization on the liquid medium.

As one preferred embodiment, the liquid medium includes 35 g/L of sucrose, 1.2 g/L of a WPM medium, 1 g/L of a N6 medium, 50 mg/L of ascorbic acid, 225 mg/L of citric acid, and 3 mg/L of indolebutyric acid.

As yet another preferred embodiment, the liquid medium includes 45 g/L of sucrose, 1.28 g/L of a B5 medium, 0.905 g/L of a ½ MS medium, 4.2 mg/L of 6-benzylaminoadenine, 3 mg/L of naphthylacetic acid, 0.8 mg/L of gibberellin, 0.6 mg/L of indoleacetic acid, and 0.6 mg/L of indolebutyric acid.

As yet another preferred embodiment, the liquid medium includes 35 g/L of sucrose, 1.35 g/L of a WPM medium, 1 g/L of a N6 medium, 5 mg/L of naphthylacetic acid, 1 mg/L of kinetin, and 0.5 mg/L of indolebutyric acid.

The adventitious roots cultured in the liquid medium in the above preferred embodiments have a best combination of the growth multiple of adventitious roots and the total saponin content.

It should be noted that in the present disclosure, the WPM medium, the B5 medium, the N6 medium, the ½ MS medium, and the like are known in the art.

½ MS Medium

Ingredients are as follows: 950 mg/L of potassium nitrate, 825 mg/L of ammonium nitrate, 220 mg/L of calcium chloride dihydrate, 185 mg/L of magnesium sulfate, 85 mg/L of potassium dihydrogen phosphate, 11.15 mg/L of manganese sulfate, 4.3 mg/L of zinc sulfate, 3.1 mg/L of boric acid, 0.415 mg/L of potassium iodide, 0.125 mg/L of sodium molybdate, 0.0125 mg/L of copper sulfate, 0.0125 mg/L of cobalt chloride, 37.3 mg/L of disodium ethylenediamine tetraacetate, 27.8 mg/L of ferrous sulfate, 100 mg/L of inositol, 2 mg/L of glycine, 0.5 mg/L of hydrochloric acid, 0.5 mg/L of pyridoxine hydrochloride, and 0.1 mg/L of thiamine hydrochloride.

B5 Medium

Ingredients are as follows: 2500 mg/L of potassium nitrate $KNO_3$, 250 mg/L of $MgSO_4 \cdot 7H_2O$, 150 mg/L of $CaCl_2 \cdot 2H_2O$, 134 mg/L of $(NH_4)_2SO_4$, 150 mg/L of $NaH_2PO_4 \cdot H_2O$, 0.75 mg/L of KI, 3.0 mg/L of $H_3BO_3$, 10 mg/L of $MnSO_4 \cdot 4H_2O$, 2.0 mg/L of $ZnSO_4 \cdot 7H_2O$, 0.25 mg/L of $Na_2MoO_4 \cdot 2H_2O$, 0.025 mg/L of $CoCl_2 \cdot 6H_2O$, 0.025 mg/L of $CuSO_4 \cdot 5H_2O$, 37.3 mg/L of $Na_2$-EDTA, 27.8 mg/L of $FeSO_4 \cdot 7H_2O$, 100 mg/L of inositol, 1.0 mg/L of nicotinic acid, 1.0 mg/L of pyridoxine hydrochloride, and 10 mg/L of thiamine hydrochloride.

Woody Plant Medium (WPM)

Ingredients are as follows: 400 mg/L of ammonium nitrate, 556 mg/L of calcium nitrate tetrahydrate, 990 mg/L of potassium sulfate, 72 mg/L of anhydrous calcium chloride, 170 mg/L of potassium dihydrogen phosphate, 0.25 mg/L of sodium molybdate dihydrate, 180 mg/L of anhydrous magnesium sulfate, 22.4 mg/L of manganese sulfate monohydrate, 8.6 mg/L of zinc sulfate heptahydrate, 0.25 mg/L of copper sulfate pentahydrate, 27.8 mg/L of ferrous sulfate heptahydrate, 37.3 mg/L of disodium ethylenediamine tetraacetate, 100 mg/L of inositol, 1 mg/L of vitamin B1, 0.5 mg/L of nicotinic acid, 0.5 mg/L of vitamin B6, and 2 mg/L of glycine, with a pH of 5.2.

N6 Medium

Ingredients are as follows: 2800 mg/L of potassium nitrate, 463 mg/L of ammonium sulfate, 400 mg/L of potassium dihydrogen phosphate, 185 mg/L of magnesium sulfate ($MgSO_4 \cdot 7H_2O$), 165 mg/L of calcium chloride ($CaCl_2 \cdot 2H_2O$), 37.3 mg/L of disodium ethylenediamine tetraacetate, 27.8 mg/L of ferrous sulfate ($FeSO_4 \cdot 7H_2O$), 4.4 mg/L of manganese sulfate ($MnSO_4 \cdot H_2O$), 1.5 mg/L of zinc sulfate ($ZnSO_4 \cdot 7H_2O$), 1.6 mg/L of boric acid, 0.8 mg/L of potassium iodide, 1.0 mg/L of vitamin B1 (thiamine hydrochloride), 0.5 mg/L of vitamin B6 (pyridoxine hydrochloride), 0.5 mg/L of nicotinic acid, 2.0 mg/L of glycine, and 20000 mg/L of sucrose, with a pH of 5.8 at 25° C.

After the above technical solution is adopted, compared with the prior art, the present disclosure has the following beneficial effects.

1. The biological reaction device of the present disclosure is a small bioreactor with a simple structure, easy operation, and sufficient and uniform ventilation. The biological reaction device can be used to produce adventitious roots of ginseng conveniently, the adventitious roots grow quickly, the growth multiple is high, and the adventitious roots grow evenly.
2. The method for culturing adventitious roots according to the present disclosure achieves direct induction of ginseng adventitious roots by inoculating the parts of the mature ginseng into the induction medium after treatment by the one-step method without the intermediate step of callus induction, which simplifies the induction steps, shortens the induction time and reduces the pollution risk.
3. The induction medium used in the method for culturing adventitious roots according to the present disclosure includes 1-6 mg/L of naphthylacetic acid, 0.2-1 mg/L of gibberellin, 0.1-0.6 mg/L of kinetin, 0.075-1.5 g/L of citric acid, 0.03-1 g/L of ascorbic acid, 20-60 g/L of sucrose, 1-6 g/L of Phytagel, 1-4 g/L of the B5 medium and 1-2.4 g/L of the WPM medium, and the ingredients act synergistically, and the problem of direct induction of the adventitious roots from the mature ginseng by the one-step method is solved, resulting in a large number of adventitious roots.

Specific embodiments of the present disclosure will be further described below in detail in combination with the accompanying drawings.

BRIEF DESCRIPTION OF THE DRAWINGS

The drawings serving as one part of the present disclosure are intended to provide a further understanding for the present disclosure. Schematic embodiments of the present disclosure and the descriptions thereof are intended to explain the present disclosure, rather than an improper limitation of the present disclosure. Obviously, the drawings described below are merely some embodiments. On the premise of not paying inventive labor, those of ordinary skill in the art can further obtain other drawings according to these drawings. In the drawings.

wherein, 1 tank body, 2 cover body, 3 air discharge device, 4 air inlet device, 5 discharge opening, 6 air inlet pipe, 7 air filter, 8 exhaust pipe, 9 filter device, 10 viewing window, 11 handle, and 12 support foot.

DETAILED DESCRIPTION OF THE EMBODIMENTS

To make the objectives, technical solutions, and advantages of embodiments of the present disclosure clearer, the technical solutions in the embodiments will be clearly and completely described below in combination with the accompanying drawings in the embodiments of the present disclosure. The following embodiments are used to describe the present disclosure but not to limit the scope of the present disclosure.

It should be noted that a preparation method or a detection method, which is not specifically defined in the present disclosure, can be performed by using a method that can be used to achieve its purpose in the prior art of the field.

Figure 1:
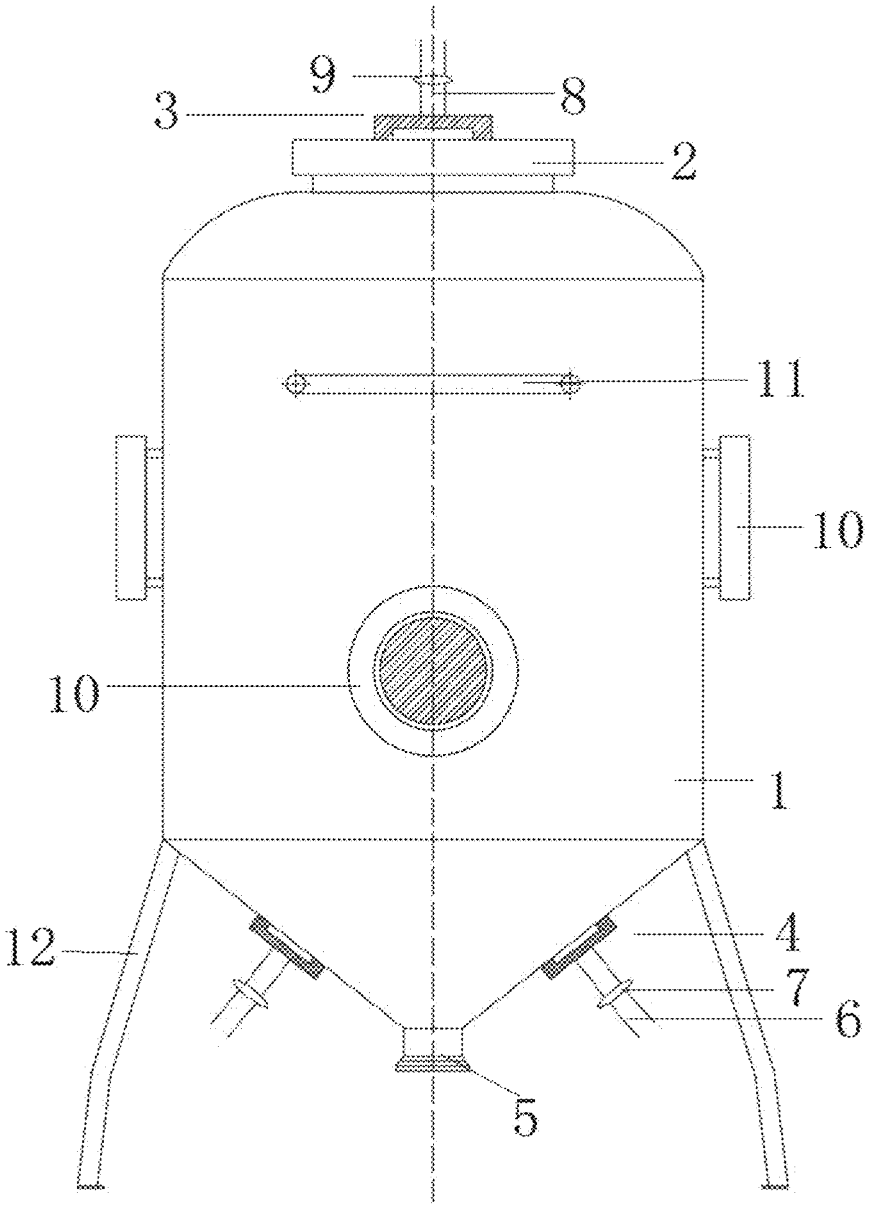
FIG. 1 is a structural schematic diagram of a biological reaction device of the present disclosure.

As shown in FIG. 1, the present disclosure provides a biological reaction device for cultivation of adventitious roots of ginseng, including a tank body 1, wherein the top of the tank body 1 is provided with a cover body 2 which can be opened and closed, and an air discharge device 3 is arranged on the cover body 2 or at the top of the tank body 1; and the bottom of the tank body 1 is provided with at least two air inlet devices 4, and air enters the tank body 1 through the air inlet devices 4.

The biological reaction device of the present disclosure is a small bioreactor with a simple structure and easy operation. The biological reaction device can be used to produce ginseng adventitious roots conveniently, and the adventitious roots grow quickly and the growth multiple is high.

In the present disclosure, the tank body 1 is hollow inside for holding a liquid medium. The biological reaction device can be made of any material suitable for manufacturing a fermenter that can be used for high-temperature sterilization, e.g., glass, stainless steel, high temperature resistant plastic, etc.; preferably, stainless steel, which is durable and has a long service life. The cover body 2 at the top of the tank body 1 can be opened or closed for adding a liquid medium into the tank body, and the cover body 2 is in sealed connection with the tank body 1 after the liquid medium is added. The bottom of the tank body 1 is provided with at least two air inlet devices 4, and sterile air is introduced into the tank body 1 from different positions, so as to ensure that a culture in the tank body can be in full contact with the air and grows evenly, which is conducive to promoting the rapid growth of adventitious roots.

A center of bottom of the tank body 1 is provided with a discharge opening 5, and the air inlet devices 4 are evenly distributed around the discharge opening 5 at intervals; and preferably, a side wall and a bottom wall of the tank body 1 are in smooth transition, and a height of the bottom wall of the tank body 1 gradually decreases from the periphery to the center to form an inverted cone with a large upper part and a small lower part. And the discharge opening 5 is formed at the lowest position of the center, and the air inlet devices 4 are evenly distributed around the discharge opening 5 at intervals on the bottom wall gradually decreasing from the periphery to the center.

In the present disclosure, the air inlet devices 4 are arranged on inclined planes of the bottom wall of the tank body 1, the bottom wall of the tank body being of the inverted cone with the large upper part and the small lower part, so that inlet air will not rise vertically. Further, two or more air inlet devices 4 are evenly distributed around the center at intervals, which is conducive to uniform distribution of air in the tank body 1 and uniform growth of adventitious roots in the tank body 1.

The biological reaction device of the present disclosure further includes a support structure for supporting the tank body 1 to be placed vertically on a plane. In particular, the support structure includes support feet 12 which are connected to or disposed integrally with a lower part of the tank body 1, and the tank body 1 is placed on a plane or platform by means of the support feet 12. Preferably, the conical bottom of the tank body 1 is located within a space enclosed by the support feet 12.

Each air inlet device 4 includes an air inlet, an air inlet pipe 6 and an air filter 7; the air inlet is located on the bottom wall of the tank body 1, the air inlet pipe 6 is connected to the air inlet in sealing manner, and the air filter 7 is disposed on the air inlet pipe 6 to filter air passing through the air inlet pipe 6.

The air discharge device 3 includes an exhaust port, an exhaust pipe 8 and a filter device 9, the exhaust port is arranged on the cover body 2 or on the top of the tank body 1, the exhaust pipe 8 is connected with the exhaust port in sealing manner, and a filter device 9 is disposed on the exhaust pipe 8; and preferably, the filter device 9 is the air filter 7 or a liquid filter.

As one preferred embodiment, the exhaust port is formed in the center of the cover body 2.

In the above solution, when the filter device 9 disposed on the exhaust pipe 8 is the air filter 7, external air can be prevented from entering the tank body 1 from the top, ensuring a sterile culture environment inside the tank body 1. In addition, liquid can be added from the top when the filter device 9 on the exhaust pipe 8 is replaced with a liquid filter.

An inoculation port is arranged on the cover body 2 or on the top of the tank body 1 for inoculation.

The tank body 1 is provided with a plurality of viewing windows 10 of transparent; and the viewing windows 10 are arranged on a side wall of a middle part and/or a lower part of the tank body 1.

When the tank body 1 is made of opaque stainless steel, the interior of the tank body 1 can be viewed from different angles through the plurality of the viewing windows 10 of transparent arranged at different positions to timely grasp the growth of ginseng adventitious roots inside the tank body 1.

The tank body 1 is also provided with a handle 11; and preferably, at least two handles 11 are provided.

The handles 11 arranged on the tank body 1 may be symmetrically arranged, which is convenient for users to conveniently take and move the biological reaction device.

Embodiment 1

(1) Induction of Adventitious Roots

Rhizomes and adventitious roots on rhizomes were removed from 20-year-old wild ginseng, leaving the taproots. The taproots were washed and sterilized, cut into slices having a width of 0.6 cm, a length of 0.7 cm, and a thickness of 0.3 mm, and inoculated into an induction medium for dark culture at 22±1° C. for 4-5 weeks to induce wild ginseng adventitious roots; wherein the induction medium includes 4 mg/L of naphthylacetic acid, 0.6 mg/L of gibberellin, 0.4 mg/L of kinetin, 0.1 g/L of citric acid, 0.05 g/L of ascorbic acid, 30 g/L of sucrose, 3 g/L of Phytagel, 1.55 g/L of a B5 medium and 1.21 g/L of a WPM medium, with a pH of 5.8.

(2) Subculture of Adventitious Roots the wild ginseng adventitious roots obtained in the step (1) were inoculated into the same induction medium as that in the step (1) for dark culture under the same conditions for 4-5 weeks.

(3) Culture of Adventitious Roots in a Shake Flask the ginseng adventitious roots obtained in the step (2) were cut into tissue of about 1 cm in length, and were inoculated into a shake flask containing a liquid medium for dark culture at 110 rpm at 22±1° C. for 3-4 weeks; wherein the liquid medium contains 4 mg/L of indolebutyric acid, 2.3 g/L of a ½ MS medium and 30 g/L of sucrose, with a pH of 5.8.

(4) Culture of Adventitious Roots in a Biological Reaction Device a liquid medium was added into a tank body of the biological reaction device, wherein a volume of the liquid medium in the biological reaction device is 70% of a volume of the biological reaction device; and the liquid medium was sterilized at 121° C. for 20 min for standby application; wherein the liquid medium contains 4 mg/L of indolebutyric acid, 2.3 g/L of a ½ MS medium and 30 g/L of sucrose, with a pH of 5.8.

The adventitious roots obtained in the step (3) were cut into tissue of about 1 cm in length, and inoculated into the liquid medium of the biological reaction device at an inoculation amount of 0.8%, the biological reaction device being fed with air at an air feeding amount of 0.1 vvm, for dark culture at 22±1° C. for 3-4 weeks to obtain adventitious roots.

Figure 2:
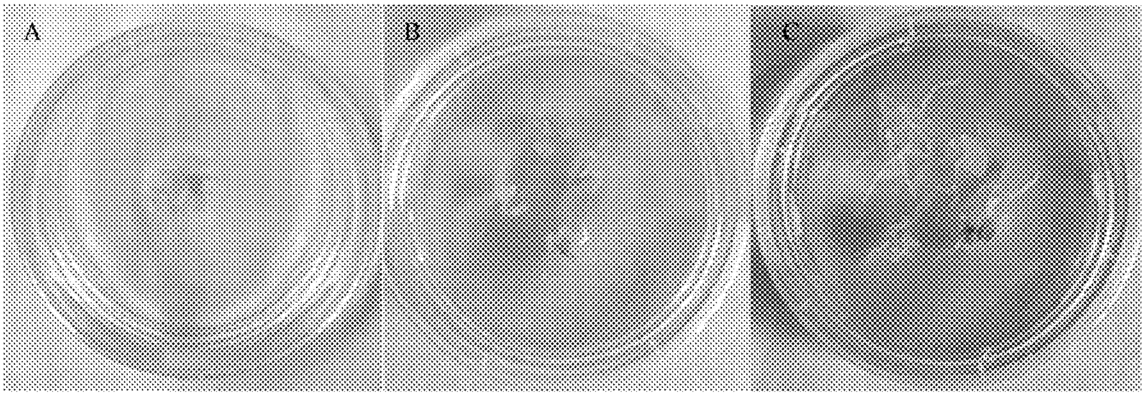
FIG. 2 is a schematic diagram of induction of adventitious roots by using an induction medium in Embodiment 1 of the present disclosure.

In this embodiment, the adventitious roots produced on the induction medium in the step (1) are shown in FIG. 2, wherein A is a photograph of 1 week of culture, B is a photograph of 3 weeks of culture, and C is a photograph of 5 weeks of culture. It can be seen that after 5 weeks, adventitious roots were directly induced on the mature wild ginseng slices.

Embodiment 2

(1) Induction of Adventitious Roots

Rhizomes of 6-year-old garden ginseng were washed and sterilized, cut into slices having a width of 0.5 cm, a length of 0.6 cm, and a thickness of 0.3 mm, and inoculated into an induction medium for dark culture at 22±1° C. for 4-5 weeks to induce adventitious roots; wherein the induction medium includes 6 mg/L of naphthylacetic acid, 0.2 mg/L of gibberellin, 0.4 mg/L of kinetin, 1.2 g/L of citric acid, 0.1 g/L of ascorbic acid, 20 g/L of sucrose, 5 g/L of Phytagel, 4 g/L of a B5 medium and 1.8 g/L of a WPM medium, with a pH of 5.6.

(2) Subculture of Adventitious Roots the adventitious roots obtained in the step (1) were inoculated into the same induction medium as that in the step (1) for dark culture under the same conditions for 4-5 weeks.

(3) Culture of Adventitious Roots in a Shake Flask the ginseng adventitious roots obtained in the step (2) were inoculated into a shake flask containing a liquid medium for dark culture at 120 rpm at 22±1° C. for 3-4 weeks; wherein the liquid medium contains 4 mg/L of indolebutyric acid, 0.1 g/L of citric acid, 0.05 g/L of ascorbic acid, a ½ MS medium and 30 g/L of sucrose, with a pH of 5.6.

(4) Culture of Adventitious Roots in a Biological Reaction Device a liquid medium was added into a tank body of the biological reaction device, wherein a volume of the liquid medium in the biological reaction device is 40% of a volume of the biological reaction device; and the liquid medium was sterilized at 121° C. for 20 min for standby application; wherein the liquid medium contains 4 mg/L of indolebutyric acid, 0.1 g/L of citric acid, 0.05 g/L of ascorbic acid, a ½ MS medium and 30 g/L of sucrose, with a pH of 5.6.

The ginseng adventitious roots obtained in the step (3) were cut into tissue of about 1 cm in length, and inoculated into the liquid medium of the biological reaction device at an inoculation amount of 0.5%, the biological reaction device being fed with air at an air feeding amount of 0.02 vvm, for dark culture at 22±1° C. for 3-4 weeks to obtain adventitious roots.

Embodiment 3

(1) Induction of Adventitious Roots

Adventitious roots on rhizomes of 10-year-old ginseng under forest were washed and sterilized, cut into slices having a width of 0.7 cm, a length of 0.7 cm, and a thickness of 0.5 mm, and inoculated into an induction medium for dark culture at 22±1° C. for 4-5 weeks to induce adventitious roots; wherein the induction medium includes 5 mg/L of naphthylacetic acid, 1 mg/L of gibberellin, 0.1 mg/L of kinetin, 0.075 g/L of citric acid, 0.03 g/L of ascorbic acid, 40 g/L of sucrose, 4 g/L of Phytagel, 2 g/L of a B5 medium and 1 g/L of a WPM medium, with a pH of 6.0.

(2) Subculture of Adventitious Roots the adventitious roots obtained in the step (1) were inoculated into the same induction medium as that in the step (1) for dark culture under the same conditions for 4-5 weeks.

(3) Culture of Adventitious Roots in a Shake Flask the ginseng adventitious roots obtained in the step (2) were inoculated into a shake flask containing a liquid medium for dark culture at 120 rpm at 22±1° C. for 3-4 weeks; wherein the liquid medium contains 4 mg/L of indolebutyric acid, 0.1 g/L of citric acid, 0.05 g/L of ascorbic acid, a WPM medium and 30 g/L of sucrose, with a pH of 6.0.

(4) Culture of Adventitious Roots in a Biological Reaction Device a liquid medium was added into a tank body of the biological reaction device, wherein a volume of the liquid medium in the biological reaction device is 60% of a volume of the biological reaction device; and the liquid medium was sterilized at 121° C. for 20 min for standby application; wherein the liquid medium contains 4 mg/L of indolebutyric acid, 0.1 g/L of citric acid, 0.05 g/L of ascorbic acid, a WPM medium and 30 g/L of sucrose, with a pH of 6.0.

The ginseng adventitious roots obtained in the step (3) were cut into tissue of about 2 cm in length, and inoculated into the liquid medium of the biological reaction device at an inoculation amount of 1%, the biological reaction device being fed with air at an air feeding amount of 0.2 vvm, for dark culture at 22±1° C. for 3-4 weeks to obtain adventitious roots.

Embodiment 4

(1) Induction of Adventitious Roots

Taproots of 15-year-old transplant wild ginseng were washed and sterilized, cut into slices having a width of 0.5 cm, a length of 0.6 cm, and a thickness of 0.4 mm, and inoculated into an induction medium for dark culture at 22±1° C. for 4-5 weeks to induce ginseng adventitious roots; wherein the induction medium includes 1 mg/L of naphthylacetic acid, 0.5 mg/L of gibberellin, 0.6 mg/L of kinetin, 1.5 g/L of citric acid, 1 g/L of ascorbic acid, 50 g/L of sucrose, 6 g/L of Phytagel, 1 g/L of a B5 medium and 2.4 g/L of a WPM medium, with a pH of 5.7.

(2) Subculture of Adventitious Roots the ginseng adventitious roots obtained in the step (1) were inoculated into the same induction medium as that in the step (1) for dark culture under the same conditions for 4-5 weeks.

(3) Culture of Adventitious Roots in a Shake Flask the ginseng adventitious roots obtained in the step (2) were inoculated into a shake flask containing a liquid medium for dark culture at 120 rpm at 22±1° C. for 3-4 weeks; wherein the liquid medium contains 4 mg/L of indolebutyric acid, 0.1 g/L of citric acid, 0.05 g/L of ascorbic acid, a B5 medium and 30 g/L of sucrose, with a pH of 5.7.

(4) Culture of Adventitious Roots in a Biological Reaction Device a liquid medium was added into a tank body of the biological reaction device, wherein a volume of the liquid medium in the biological reaction device is 30% of a volume of the biological reaction device; and the liquid medium was sterilized at 121° C. for 20 min for standby application; wherein the liquid medium contains 4 mg/L of indolebutyric acid, 0.1 g/L of citric acid, 0.05 g/L of ascorbic acid, a B5 medium and 30 g/L of sucrose, with a pH of 5.7.

The ginseng adventitious roots obtained in the step (3) were cut into tissue of about 1 cm in length, and inoculated into the liquid medium of the biological reaction device at an inoculation amount of 0.2%, the biological reaction device being fed with air at an air feeding amount of 0.05 vvm, for dark culture at 22±1° C. for 3-4 weeks to obtain adventitious roots.

Embodiment 5

(1) Induction of Adventitious Roots

Rhizomes and adventitious roots on rhizomes were removed from centennial wild ginseng, taproots were washed and sterilized, cut into slices having a width of 0.6 cm, a length of 0.7 cm, and a thickness of 0.3 mm, and inoculated into an induction medium for dark culture at 22±1° C. for 4-5 weeks to induce ginseng adventitious roots; wherein the induction medium includes 4 mg/L of naphthylacetic acid, 0.6 mg/L of gibberellin, 0.4 mg/L of kinetin, 0.1 g/L of citric acid, 0.05 g/L of ascorbic acid, 30 g/L of sucrose, 3 g/L of Phytagel, 1.55 g/L of a B5 medium and 1.21 g/L of a WPM medium, with a pH of 5.8.

(2) Subculture of Adventitious Roots the ginseng adventitious roots obtained in the step (1) were inoculated into the same induction medium as that in the step (1) for dark culture under the same conditions for 4-5 weeks;

(3) Culture of Adventitious Roots in a Shake Flask the ginseng adventitious roots obtained in the step (2) were inoculated into a shake flask containing a liquid medium for dark culture at 120 rpm at 22±1° C. for 3-4 weeks; wherein the liquid medium contains 4 mg/L of indolebutyric acid, 0.1 g/L of citric acid, 0.05 g/L of ascorbic acid, a ½ MS medium and 30 g/L of sucrose, with a pH of 5.8.

(4) Culture of Adventitious Roots in a Biological Reaction Device a liquid medium was added into a tank body of the biological reaction device, wherein a volume of the liquid medium in the biological reaction device is 75% of a volume of the biological reaction device; and the liquid medium was sterilized at 121° C. for 20 min for standby application; wherein the liquid medium contains 4 mg/L of indolebutyric acid, 0.1 g/L of citric acid, 0.05 g/L of ascorbic acid, a ½ MS medium and 30 g/L of sucrose, with a pH of 5.8.

The ginseng adventitious roots obtained in the step (3) were cut into tissue of about 1 cm in length, and inoculated into the liquid medium of the biological reaction device at an inoculation amount of 3%, the biological reaction device being fed with air at an air feeding amount of 0.5 vvm, for dark culture at 22±1° C. for 3-4 weeks to obtain adventitious roots.

Comparative Example 1

This comparative example differed from Embodiment 1 in that the induction medium used was different and the other steps were carried out with reference to Embodiment 1. The induction medium in this comparative example includes: 30 g/L of sucrose, 0.5 mg/L of kinetin, 3 mg/L of indolebutyric acid, 1.5 mg/L of 2,4-dichlorophenoxyacetic acid, a ½ MS medium, and 3 g/L of Phytagel, with a pH of 5.8.

Figure 3:
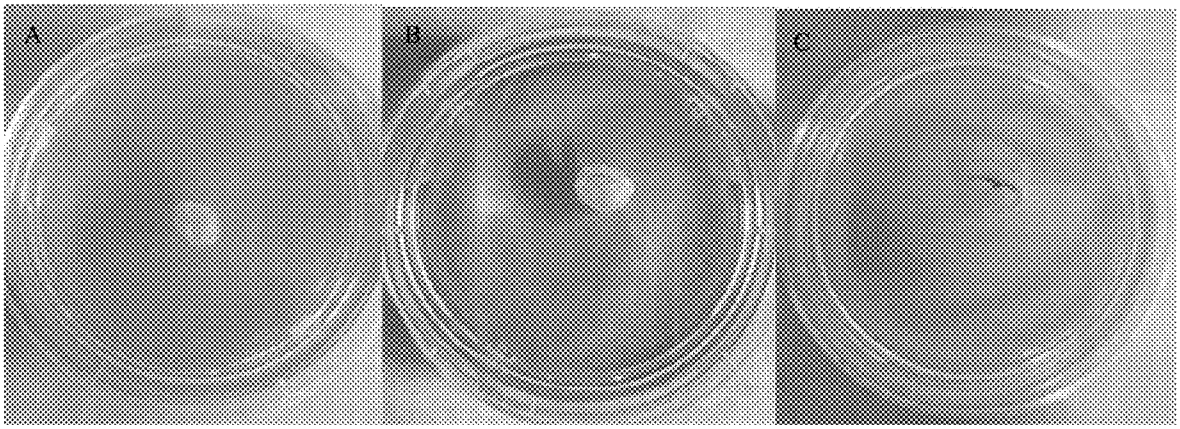
FIG. 3 is a schematic diagram of induction of adventitious roots by using an induction medium in Comparative example 1.

The adventitious roots produced on the induction medium in the step (1) of this comparative example are shown in FIG. 3, wherein A is a photograph of 1 week of culture, B is a photograph of 3 weeks of culture, and C is a photograph of 5 weeks of culture. It can be seen that after 5 weeks, adventitious roots cannot be directly induced from mature wild ginseng slices by using the medium in Comparative example 1.

Comparative Example 2

This comparative example differed from Embodiment 1 in that the induction medium used was different and the other steps were carried out with reference to Embodiment 1. The induction medium in this comparative example includes: 30 g/L of sucrose, 0.5 mg/L of kinetin, 3 mg/L of indolebutyric acid, a ½ MS medium, and 3 g/L of Phytagel, with a pH of 5.8.

As a result, similar to that shown in the picture in Comparative example 1, adventitious roots cannot be directly induced from mature wild ginseng slices.

Comparative Example 3

This comparative example differed from Embodiment 1 in that the induction medium used was different and the other steps were carried out with reference to Embodiment 1. The induction medium in this comparative example includes: 30 g/L of sucrose, 0.5 mg/L of kinetin, 3 mg/L of indoleacetic acid, WPM, and 3 g/L Phytagel, with a pH of 5.8.

Results: in the first week, the whole body turned yellow, in the third week, the color deepened, and the middle part began to turn brown, and in the fifth week, all became brown and withered.

Comparative Example 4

In this comparative example, the difference from Embodiment 1 was that the biological reaction device employed was different in that only one air vent was formed in the center of the bottom of the tank body, one air inlet device was provided, and the bottom wall of the tank body was of a downward concave circular arc; and other conditions were the same as those in Embodiment 1.

The ginseng adventitious roots were cultured by using the biological reaction device of the present disclosure (i.e., a 5 L fermenter of the present disclosure) and the biological reaction device in this Comparative example 4 (with a volume of 5 L), respectively, and the growth results of the ginseng adventitious roots in the medium are as follows:

TABLE 1

| Experimental group | Adventitious root growth multiple |
|---|---|
| Comparative example 4 | 8 |
| Embodiment 1 | 14 |

Thus, under the same conditions, the weight gain multiple of adventitious roots is higher, and the growth is better by using the biological reaction device of the present disclosure, which is beneficial to improving the efficiency and obtaining higher content of ginsenoside.

Test Example 1 Screening of Liquid Medium

In order to increase the content of ginsenoside in the ginseng adventitious roots, a liquid medium was further subjected to screening optimization.

A culture method in this test example refers to the method in Embodiment 1 with the difference that:

1. the liquid medium in Embodiment 1 was replaced with a plurality of liquid media in this test example described below, and
2. the step (4) was omitted, and liquid culture in a shake flask was used for examination.

The content of ginsenoside in the ginseng adventitious roots was then detected.

A detection method of ginsenoside in the ginseng adventitious roots includes:

(1) Principle

After pretreatment such as extraction, a sample was separated by a C18 chromatographic column, and detected by a HPLC-UV detector, and the content of ginsenoside components was determined quantitatively by an external standard method.

(2) Reagents

Methanol ($CH_4O$): chromatographically pure, and acetonitrile ($C_6H_{11}N$): chromatographically pure Standard reagent: ginsenosides Re, Rg1, Ra3, Rb1, Rf, Rb2, Rb3, F3, Rg2, Rd, and F1.

(3) Analysis Steps

Preparation of Adventitious Root Test Solution:

about 6 g (accurate to 0.01 g) of uniformly mixed adventitious roots to be tested was taken, ground in a 150 mL mortar, transferred to a 50 ml centrifuge tube, mixed with 10 ml of water, wall broken on a ultrasonic cell disruptor at 400 W for 3 min, and frozen in a refrigerator at −18° C. for 3 h. The frozen material was lyophilized in a lyophilizer for 48 h until there were no water beads outside a cup.

The above sample was ground in a mortar, 50 mg of the ground sample was accurately weighed to be placed in a 10 ml centrifuge tube, a 70% methanol solution was added, and vortex was conducted. Ultrasonic treatment was conducted on an ultrasonic oscillator for 10 min, the above operation was conducted repeatedly twice, and filtration was conducted for later use.

Standard Preparation:

Preparation of stock solution (0.8 mg/ml): 8.00 mg of ginsenosides Re, Rb1, Rg1, Rd, Rf, F3, Rk2, Rb2, Rb3, Rg2, and F1, which are 11 standards in total, were respectively weighed to be placed in a 10 ml volumetric flask, and the volume was made up to a constant volume with superior pure methanol.

Preparation of use solution (32 μg/ml): 1 ml of the stock solution (0.8 mg/ml) was accurately pipetted into a 25 ml volumetric flask, and made up to a constant volume with superior pure methanol, and filtered through a 0.22 μm organic filter membrane for later use.

(4) Instrument Reference Conditions

A) Chromatographic column: a C18 column with a column length of 150 mm, a column internal diameter of 4.6 mm, and a column packing particle size of 5 μm, or equivalent;

B) Mobile phase: a: acetonitrile, and b: water filtered through a 0.45 μm microporous filter membrane;

C) Flow rate: 0.7 mL/min; gradient elution procedure: 0-13 min, 23-46% acetonitrile, with a volume flow rate of 0.7 mL/min; 13-33 min, 46-68% acetonitrile, with a volume flow rate of 0.7 mL/min; 33-46.5 min, 68-85% acetonitrile, with a volume flow rate of 0.7 mL/min;

D) Column temperature: 30° C.;

E) Detection wavelength: 203 nm; and

F) Injection volume: 10 μL.

(5) Expression of Analysis Results

The content of ginsenoside components in the sample is calculated according to a formula (1):

$$X = \frac{A1}{A2} \times \frac{\rho \times V}{M} \quad (1)$$

in the formula:

X—the content of ginsenoside components in a sample in milligrams per kilogram (mg/kg) or milligrams per liter (mg/L);

A1—peak area of ginsenoside components in a sample

A2—peak area of ginsenoside components in a standard p—concentration of ginsenoside components in a standard (μg/ml)

V—final constant volume of a sample solution in milliliters (mL);

M—sample mass in grams (g);

The content of ginsenoside in the sample is the sum of those detected in the components.

The growth multiple is calculated as follows:

Growth multiple=weight of adventitious roots after growth/weight of inoculated adventitious root seeds.

1. Liquid Medium 1

A liquid medium 1 includes: 15-50 g/L of sucrose, 0.6-2.4 g/L of a WPM medium, 1-2 g/L of a N6 medium, 0-150 mg/L of ascorbic acid (Vc), 0-225 mg/L of citric acid, and 0-7 mg/L of indolebutyric acid (IBA), with a pH of 5.8.

TABLE 2

| Experimental group | Sucrose (g/l) | N6 medium (g/l) | WPM medium (g/l) | Vc (mg/L) | Citric acid (mg/L) | IBA (mg/L) | Growth multiple | Ginsenoside content (mg/kg) |
|---|---|---|---|---|---|---|---|---|
| 1 | 15 | 2 | 2.4 | 150 | 150 | 7 | 4.7 | 9310.8 |
| 2 | 20 | 2 | 2.4 | 150 | 0 | 6 | 3.2 | 7999.3 |
| 3 | 25 | 2 | 1.8 | 100 | 150 | 5 | 12.8 | 9458.8 |
| 4 | 30 | 2 | 1.8 | 100 | 0 | 4 | 8 | 9923.9 |
| 5 | 35 | 1 | 1.2 | 50 | 225 | 3 | 11.5 | 16622.1 |
| 6 | 40 | 1 | 1.2 | 50 | 75 | 2 | 12.5 | 11733.5 |
| 7 | 45 | 1 | 0.6 | 0 | 225 | 1 | 8.4 | 10453.6 |
| 8 | 50 | 1 | 0.6 | 0 | 75 | 0 | 1.4 | 9607.3 |

As can be seen in Table 2 above, the growth multiple of adventitious roots was higher, and the total amount of ginsenosides detected was higher by using the liquid media 1 with the ratios in Experimental groups 5-7, with a best combination of the growth multiple of adventitious roots and the ginsenosides content in Experimental group 5.

2. Liquid medium 2

A liquid medium 2 includes: 10-55 g/L of sucrose, 0.3-1.2 g/L of a ½ MS medium, 0.6-1.6 g/L of a B5 medium, 0-5.4 mg/L of indoleacetic acid (IAA), 0-5.4 mg/L of indolebutyric acid (IBA), 0-5.4 mg/L of naphthylacetic acid (NAA), 0-5.4 mg/L of 6-benzylaminoadenine (6BA), and 0-8 mg/L of gibberellin (GA), with a pH of 5.8.

TABLE 3

| Experimental group | Sucrose (g/l) | ½ MS (g/l) | B5 medium (g/l) | IAA (mg/l) | IBA (mg/l) | NAA (mg/l) | 6BA (mg/l) | GA (mg/l) | Growth multiple | Ginsenoside content (mg/kg) |
|---|---|---|---|---|---|---|---|---|---|---|
| 1 | 10 | 0.405 | 0.78 | 3 | 5.4 | 4.2 | 3.6 | 1.6 | 2.7 | 7157.77 |
| 2 | 50 | 1.005 | 1.38 | 2.4 | 5.4 | 3.6 | 1.8 | 6.4 | 1.7 | 9773.01 |
| 3 | 55 | 0.305 | 0.68 | 3.6 | 1.8 | 0.6 | 4.2 | 4 | 1.8 | 7908.18 |
| 4 | 45 | 0.905 | 1.28 | 0.6 | 0.6 | 3 | 4.2 | 0.8 | 6.7 | 15878.75 |
| 5 | 15 | 0.805 | 1.18 | 4.2 | 0 | 2.4 | 2.4 | 8 | 1.7 | 16575 |
| 6 | 45 | 0.705 | 1.08 | 4.8 | 3.6 | 1.8 | 0 | 0 | 9.3 | 10523.13 |
| 7 | 20 | 1.205 | 1.58 | 1.8 | 2.4 | 0 | 1.2 | 2.4 | 3.9 | 6784.19 |
| 8 | 35 | 0.505 | 0.88 | 1.2 | 1.2 | 5.4 | 0.6 | 4.8 | 1.5 | 11589.18 |
| 9 | 30 | 1.105 | 1.48 | 5.4 | 3 | 5.4 | 5.4 | 3.2 | 6.3 | 8850.39 |
| 10 | 25 | 0.605 | 0.98 | 0 | 4.8 | 1.2 | 4.8 | 5.6 | 1.9 | 7516.73 |

As can be seen in Table 3 above, the growth multiple of adventitious roots was higher, and the total amount of ginsenosides detected was higher by using the liquid media 2 with the ratios in Experimental groups 4 and 6, with a best combination of the growth multiple of adventitious roots and the ginsenosides content in Experimental group 4.

3. Liquid Medium 3

A liquid medium 3 includes: 35 g/L of sucrose, 1.35 g/L of a WPM medium, 1 g/L of a N6 medium, 0-1.8 mg/L of indolebutyric acid (IBA), 1-6 mg/L of naphthylacetic acid (NAA), and 0.2-1.2 mg/L of kinetin (KT), with a pH of 5.8.

TABLE 4

| Experimental group | Sucrose (g/l) | WPM (g/l) | N6 (g/l) | IBA (mg/L) | NAA (mg/l) | KT (mg/l) | Growth multiple | Ginsenoside content (mg/kg) | Culture day |
|---|---|---|---|---|---|---|---|---|---|
| 1 | 35 | 1.35 | 1 | 1 | 2 | 1.2 | 6.9 | 7727.6 | 33 |
| 2 | 35 | 1.35 | 1 | 0.2 | 4 | 1.2 | 8.2 | 9123.5 | 42 |
| 3 | 35 | 1.35 | 1 | 1 | 6 | 0.2 | 9.5 | 9977.3 | 33 |
| 4 | 35 | 1.35 | 1 | 0.6 | 2 | 0.2 | 9.7 | 10045.2 | 42 |
| 5 | 35 | 1.35 | 1 | 0 | 4 | 0.2 | 7.8 | 8745.6 | 33 |
| 6 | 35 | 1.35 | 1 | 0.4 | 6 | 0.4 | 8.8 | 9576.1 | 30 |
| 7 | 35 | 1.35 | 1 | 0.8 | 2 | 1 | 10.1 | 11457.3 | 30 |
| 8 | 35 | 1.35 | 1 | 0.4 | 4 | 1 | 10.5 | 11948.1 | 39 |
| 9 | 35 | 1.35 | 1 | 0.2 | 6 | 1.2 | 8.5 | 9011.4 | 30 |
| 10 | 35 | 1.35 | 1 | 1 | 1 | 0.8 | 9.5 | 11387.5 | 30 |
| 11 | 35 | 1.35 | 1 | 0.6 | 3 | 0.8 | 12.3 | 14567.2 | 39 |
| 12 | 35 | 1.35 | 1 | 0.2 | 5 | 1 | 13.1 | 15432.7 | 36 |
| 13 | 35 | 1.35 | 1 | 0 | 1 | 0.6 | 5.4 | 6741.2 | 45 |

TABLE 4-continued

| Experimental group | Sucrose (g/l) | WPM (g/l) | N6 (g/l) | IBA (mg/L) | NAA (mg/l) | KT (mg/l) | Growth multiple | Ginsenoside content (mg/kg) | Culture day |
|---|---|---|---|---|---|---|---|---|---|
| 14 | 35 | 1.35 | 1 | 0.8 | 3 | 0.6 | 8.5 | 8764.1 | 35 |
| 15 | 35 | 1.35 | 1 | 0.4 | 5 | 0.8 | 11.9 | 10743.4 | 45 |
| 16 | 35 | 1.35 | 1 | 1.8 | 1 | 0.4 | 12.0 | 11547.3 | 36 |
| 17 | 35 | 1.35 | 1 | 0.8 | 3 | 0.4 | 12.1 | 12634.1 | 42 |
| 18 | 35 | 1.35 | 1 | 0.6 | 5 | 0.6 | 12.5 | 12749.5 | 45 |

As can be seen from Table 4 above, on the basis of determining the amount of sucrose, WPM and N6, the effects of plant hormones IBA, NAA and KT on the yield of adventitious roots and the content of ginsenosides were examined at different addition amounts, so as to select the appropriate plant hormones and their ratios. As can be seen from the table, the growth multiple of adventitious roots and the total ginsenosides content were better under the formulas of Experimental groups 4, 7-8, 10-12 and 15-18, with a best combination of the growth multiple of adventitious roots and the total ginsenosides content according to the conditions in Experimental group 12.

The inventors further use the liquid medium 1, the liquid medium 2 or the liquid medium 3 to culture the ginseng adventitious roots by using the above biological reaction device, and the growth multiple of the obtained adventitious roots is high.

The above description is only preferred embodiments of the present disclosure, and is not intended to limit the present disclosure in any form. Although the present disclosure has been disclosed above with the preferred embodiments, it is not intended to limit the present disclosure. Any person familiar with this patent can make some changes or modifications to equivalent embodiments by using the technical contents mentioned above without departing from the scope of the technical solution of the present disclosure. However, any simple changes, equivalent variations and modifications made to the above embodiments according to the technical essence of the present disclosure without departing from the content of the technical solution of the present disclosure are still within the scope of the solution of the present disclosure.

What is claimed is:

1. A method for culturing adventitious roots of ginseng by using a biological reaction device, said method comprising:

(1) washing and disinfecting mature ginseng, cutting the mature ginseng disinfected into ginseng slices, and inoculating the ginseng slices into an induction medium to induce adventitious roots of ginseng;

(2) re-inoculating the adventitious roots of ginseng obtained in step (1) into an induction medium for subculture and propagation;

(3) inoculating the adventitious roots of ginseng obtained in step (2) into a shake flask containing a liquid medium for dark culture; and then (4) inoculating the adventitious roots of ginseng obtained in step (3) into the biological reaction device containing a liquid medium for culture to obtain adventitious roots of ginseng.

2. The method for culturing the adventitious roots of ginseng by using the biological reaction device according to claim 1, wherein in the steps (1) and (2), the induction medium comprises 1-6 mg/L of naphthylacetic acid, 0.1-0.6 mg/L of kinetin, 0.2-1 mg/L of gibberellin, 0.075-1.5 g/L of citric acid, 0.03-1 g/L of ascorbic acid, 20-60 g/L of sucrose, 1-6 g/L of Phytagel, 1-4 g/L of a B5 medium and 1-2.4 g/L of a WPM medium.

3. The method for culturing the adventitious roots of ginseng by using the biological reaction device according to claim 1, wherein in the steps (3) and (4), the liquid medium includes a basic medium selected one or more one medium from a group containing a B5 medium, a WPM medium and a ½ MS medium, and 4 mg/L of indolebutyric acid, and 30 g/L of sucrose.

4. The method for culturing the adventitious roots of ginseng by using the biological reaction device according to claim 1, wherein in the step (3), a volume of a sterilized liquid medium is 20%-80% of a volume of the biological reaction device.

5. The method for culturing the adventitious roots of ginseng by using the biological reaction device according to claim 3, wherein the liquid medium further comprises 0.1 g/L of citric acid, and 0.05 g/L of ascorbic acid.

6. The method for culturing the adventitious roots of ginseng by using the biological reaction device according to claim 1, wherein the volume of sterilized liquid medium is 30%-70% of a volume of the biological reaction device.

7. The method for culturing the adventitious roots of ginseng by using the biological reaction device according to claim 1, wherein the adventitious roots are inoculated into the liquid medium at an inoculation amount of 0.2%-3%.

8. The method for culturing the adventitious roots of ginseng by using the biological reaction device according to claim 1, wherein the biological reaction device is fed with filtered air by air inlet devices at an air feeding amount of 0.02-0.5 vvm.

9. The method for culturing the adventitious roots of ginseng by using the biological reaction device according to claim 1, wherein the dark culture is conducted at 22±1° C. for 4-5 weeks in the biological reaction device.

10. The method for culturing the adventitious roots of ginseng by using the biological reaction device according to claim 1, wherein the biological reaction device for cultivation of adventitious roots of ginseng, comprising:

a tank body, a cover body, being capable of being open and close and arranged on a top of the tank body;

an air discharge device, arranged on the cover body or at the top of the tank body; and at least two air inlet devices, arranged at a bottom of the tank body, and allowing air to enter an inside of the tank body through the at least two air inlet devices.

11. The method for culturing the adventitious roots of ginseng by using the biological reaction device according to claim 10, wherein a discharge opening is arranged at a center of the bottom of the tank body, and the air inlet devices are evenly distributed around the discharge opening at intervals.

12. The method for culturing the adventitious roots of ginseng by using the biological reaction device according to claim 10, wherein a height of a bottom wall of the tank body is gradually decreased from a periphery to a center to form an inverted cone, a diameter of an upper part of the inverted cone is larger than a diameter of a lower part of the inverted cone; and the discharge opening is formed at the lowest position of the center of the bottom of the tank body, and the air inlet devices are evenly distributed around the discharge opening at intervals at the bottom wall of the tank body gradually decreasing from the periphery to the center.

13. The method for culturing the adventitious roots of ginseng by using the biological reaction device according to claim 10, wherein each of the air inlet devices comprises an air inlet, an air inlet pipe and an air filter, the air inlet is located on the bottom wall of the tank body, the air inlet pipe is connected to the air inlet in sealing manner, and the air filter is disposed in the air inlet pipe to filter air passing through the air inlet pipe.

14. The method for culturing the adventitious roots of ginseng by using the biological reaction device according to claim 10, wherein the air discharge device comprises an exhaust port, an exhaust pipe and a filter device, the exhaust port is arranged on the cover body or on the top of the tank body, the exhaust pipe is connected with the exhaust port in sealing manner, and the filter device is disposed in the exhaust pipe.

15. The method for culturing the adventitious roots of ginseng by using the biological reaction device according to claim 14, wherein the filter device is an air filter or a liquid filter.

16. The method for culturing the adventitious roots of ginseng by using the biological reaction device according to claim 10, wherein the tank body is provided with a plurality of viewing windows of transparent for viewing the interior of the tank body.

17. The method for culturing the adventitious roots of ginseng by using the biological reaction device according to claim 16, wherein the viewing windows are arranged on a side wall of a middle part and/or a lower part of the tank body.

18. The method for culturing the adventitious roots of ginseng by using the biological reaction device according to claim 10, wherein the tank body is also provided with a handle.

19. The method for culturing the adventitious roots of ginseng by using the biological reaction device according to claim 18, wherein the tank body is provided with at least two handles.

* * * * *